(12) United States Patent
Serhan et al.

(10) Patent No.: US 8,267,970 B2
(45) Date of Patent: Sep. 18, 2012

(54) LAMINAR HOOK SPRING

(75) Inventors: Hassan A. Serhan, S. Easton, MA (US); Michael A. Slivka, Taunton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1250 days.

(21) Appl. No.: 11/257,732

(22) Filed: Oct. 25, 2005

(65) Prior Publication Data
US 2007/0123859 A1    May 31, 2007

(51) Int. Cl.
    *A61B 17/70*    (2006.01)
(52) U.S. Cl. .......... 606/276; 606/90; 606/246; 606/248; 606/249; 600/236; 600/237
(58) Field of Classification Search .............. 606/57, 606/282, 90, 105, 191, 206, 212, 209, 215, 606/217, 218, 219, 236, 237, 242, 60, 246–249
    See application file for complete search history.

(56) References Cited

U.S. PATENT DOCUMENTS

| | | | |
|---|---|---|---|
| 281,880 A * | 7/1883 | Hubbell | 600/219 |
| 1,025,362 A * | 5/1912 | Beuoy | 606/210 |
| 1,389,436 A * | 8/1921 | Cameron | 600/219 |
| 1,450,419 A * | 4/1923 | Heidbrink | 600/237 |
| 2,217,968 A * | 10/1940 | Radcliff | 606/198 |
| 2,238,563 A * | 4/1941 | Jacques | 27/21.1 |
| 3,241,550 A * | 3/1966 | Gelarie | 600/242 |
| 3,750,652 A * | 8/1973 | Sherwin | 606/90 |
| 3,916,880 A * | 11/1975 | Schroer | 600/205 |
| 4,611,582 A * | 9/1986 | Duff | 606/258 |
| 4,743,260 A | 5/1988 | Burton | |
| 4,841,960 A * | 6/1989 | Garner | 606/75 |
| 5,011,484 A * | 4/1991 | Breard | 606/249 |
| 5,092,866 A | 3/1992 | Breard et al. | |
| 5,180,393 A | 1/1993 | Commarmond | |
| 5,307,790 A * | 5/1994 | Byrne | 600/206 |
| 5,415,661 A * | 5/1995 | Holmes | 606/255 |
| 5,423,857 A * | 6/1995 | Rosenman et al. | 606/219 |

(Continued)

FOREIGN PATENT DOCUMENTS

WO    WO 03/015645    2/2003

(Continued)

OTHER PUBLICATIONS

International Preliminary Report on Patentability for Application No. PCT/US2006/037444 mailed May 8, 2008.

*Primary Examiner* — Eduardo C Robert
*Assistant Examiner* — Jerry Cumberledge
(74) *Attorney, Agent, or Firm* — Nutter McClennen & Fish LLP

(57) ABSTRACT

Various devices and methods are provided for spinal augmentation. In particular, the device can includes a connector element having a superior portion and an inferior portion that is adapted to support adjacent superior and inferior vertebrae and a first superior seating member and a second superior seating member associated with the connector element. The first seating member can be adapted to receive a portion of a lamina of the superior vertebra and the second seating member can be adapted to receive a portion of the lamina of the inferior vertebra. The device can have a variety of configurations, including the connector element and the first and second seating members being unitary and the first and second seating members being separately secured to the connector element.

10 Claims, 6 Drawing Sheets

U.S. PATENT DOCUMENTS

| | | | |
|---|---|---|---|
| 5,433,190 A * | 7/1995 | Sunalp | 600/236 |
| 5,496,318 A | 3/1996 | Howland et al. | |
| 5,540,688 A | 7/1996 | Navas | |
| 5,562,737 A | 10/1996 | Graf | |
| 5,609,634 A | 3/1997 | Voydeville | |
| 5,618,261 A * | 4/1997 | Nevyas | 600/236 |
| 5,620,444 A * | 4/1997 | Assaker | 606/276 |
| 5,645,599 A * | 7/1997 | Samani | 623/17.16 |
| 5,672,175 A | 9/1997 | Martin | |
| 5,683,405 A * | 11/1997 | Yacoubian et al. | 606/158 |
| 5,725,582 A | 3/1998 | Bevan et al. | |
| 5,766,004 A * | 6/1998 | Besselink et al. | 433/5 |
| 5,860,977 A | 1/1999 | Zucherman et al. | |
| 5,876,404 A | 3/1999 | Zucherman et al. | |
| 6,080,157 A * | 6/2000 | Cathro et al. | 606/279 |
| 6,136,017 A * | 10/2000 | Craver et al. | 606/205 |
| 6,241,730 B1 | 6/2001 | Alby et al. | |
| 6,267,764 B1 | 7/2001 | Elberg | |
| 6,325,805 B1 * | 12/2001 | Ogilvie et al. | 606/75 |
| 6,379,355 B1 | 4/2002 | Zucherman et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,544,169 B2 * | 4/2003 | Putrino et al. | 600/236 |
| 6,582,433 B2 * | 6/2003 | Yun | 606/249 |
| 6,626,944 B1 | 9/2003 | Taylor | |
| 6,652,534 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,702,739 B2 * | 3/2004 | Levisman | 600/217 |
| 6,743,257 B2 * | 6/2004 | Castro | 623/17.16 |
| 7,476,251 B2 * | 1/2009 | Zucherman et al. | 623/17.15 |
| 7,695,496 B2 * | 4/2010 | Labrom et al. | 606/249 |
| 2002/0072752 A1 | 6/2002 | Zucherman et al. | |
| 2002/0077702 A1 * | 6/2002 | Castro | 623/17.16 |
| 2002/0091446 A1 | 7/2002 | Zucherman et al. | |
| 2002/0099377 A1 | 7/2002 | Zucherman et al. | |
| 2002/0111679 A1 | 8/2002 | Zucherman et al. | |
| 2002/0143331 A1 | 10/2002 | Zucherman et al. | |
| 2003/0055427 A1 | 3/2003 | Graf | |
| 2003/0065330 A1 | 4/2003 | Zucherman et al. | |
| 2003/0153915 A1 | 8/2003 | Nekozuka et al. | |
| 2003/0191470 A1 * | 10/2003 | Ritland | 606/61 |
| 2003/0216736 A1 | 11/2003 | Robinson et al. | |
| 2003/0220643 A1 | 11/2003 | Ferree | |
| 2004/0002708 A1 | 1/2004 | Ritland | |
| 2004/0006343 A1 * | 1/2004 | Sevrain | 606/61 |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0087948 A1 * | 5/2004 | Suddaby | 606/61 |
| 2004/0097931 A1 | 5/2004 | Mitchell | |
| 2004/0106995 A1 | 6/2004 | Le Couedic et al. | |
| 2004/0117017 A1 | 6/2004 | Pasquet et al. | |
| 2004/0127989 A1 | 7/2004 | Dooris et al. | 623/13.17 |
| 2004/0147935 A1 * | 7/2004 | Segler | 606/90 |
| 2004/0210222 A1 * | 10/2004 | Angelucci et al. | 606/69 |
| 2004/0230192 A1 | 11/2004 | Graf | |
| 2004/0267259 A1 | 12/2004 | Mazda et al. | |
| 2005/0125063 A1 * | 6/2005 | Matge et al. | 623/17.13 |
| 2005/0192581 A1 * | 9/2005 | Molz et al. | 606/74 |
| 2005/0203512 A1 * | 9/2005 | Hawkins et al. | 606/61 |
| 2005/0203624 A1 * | 9/2005 | Serhan et al. | 623/17.11 |
| 2005/0261768 A1 * | 11/2005 | Trieu | 623/17.11 |
| 2006/0235387 A1 * | 10/2006 | Peterman | 606/61 |
| 2006/0241614 A1 * | 10/2006 | Bruneau et al. | 606/69 |
| 2006/0271044 A1 * | 11/2006 | Petrini et al. | 606/61 |
| 2006/0293662 A1 * | 12/2006 | Boyer et al. | 606/61 |
| 2008/0183209 A1 * | 7/2008 | Robinson et al. | 606/246 |

FOREIGN PATENT DOCUMENTS

| | | |
|---|---|---|
| WO | WO 03/015646 | 2/2003 |
| WO | WO 2004/024010 A1 | 3/2004 |

* cited by examiner

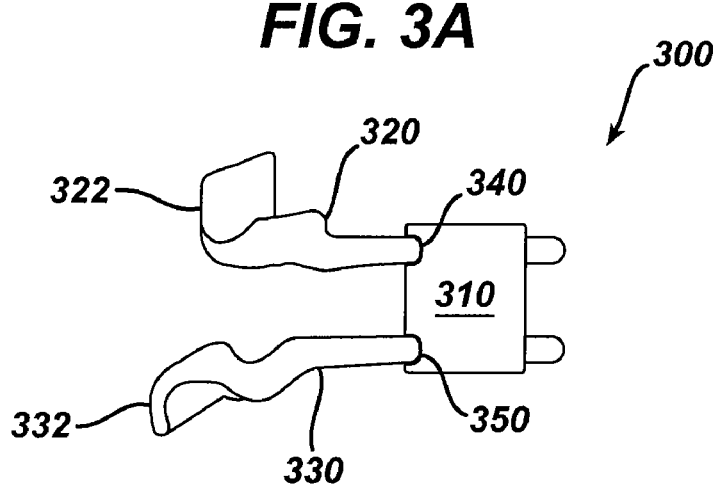
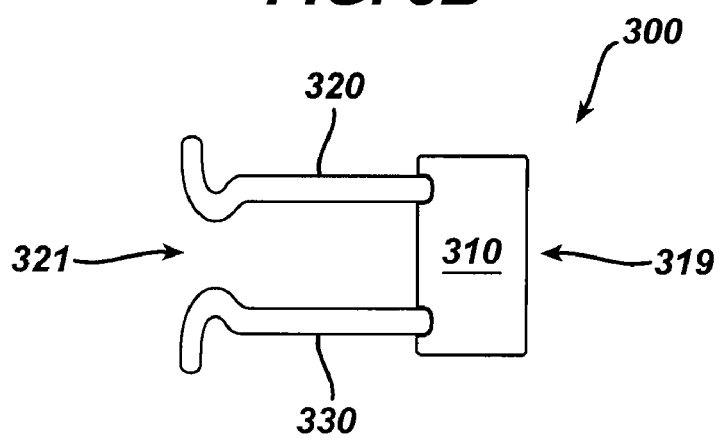
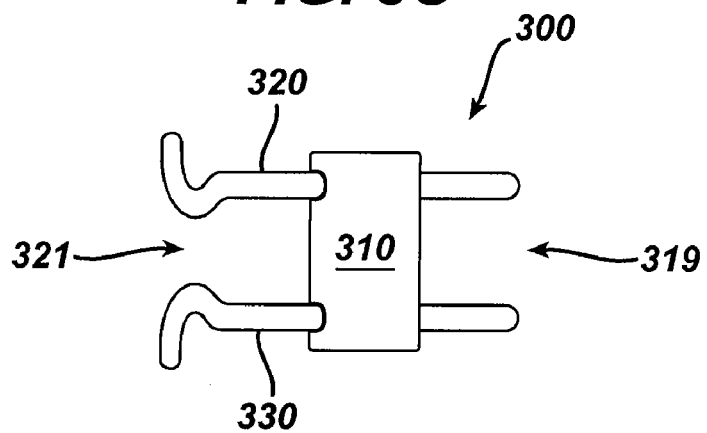

LAMINAR HOOK SPRING

BACKGROUND OF THE INVENTION

Disease, advancing age, and trauma can lead to changes in various bones, discs, joints, and ligaments of the body. Some changes and trauma often manifest themselves in the form of damage or degeneration to a spinal disc and/or the spacing between adjacent vertebral bodies. These conditions often result in chronic back pain, which can be anywhere from mild to severe. This pain can sometimes be eliminated by surgical techniques to effect spinal fusion or a dynamic solution. Spinal fusion involves joining together two adjacent vertebral bodies by fixing with hardware and/or causing bone to grow therebetween. Dynamic surgical solutions involve surgically installing devices such as artificial discs, spinous process spacers, facet joint prostheses, and flexible pedicle screw systems. Although effective, the dynamic solutions require major surgery and rigid systems, such as fusion devices, reduce mobility.

One example of a dynamic solution is a spinous process spacer attached to the spinous process of the vertebrae. These spacers are implanted with minimal destruction of tissue and without the need for pedicle screws or other devices that require bony destruction for attachment to the vertebrae. While the spinous process spacers provide some improvements over the system using pedicle screws, the spinous process is a weak structural part of the vertebrae that can be prone to breakage, especially with the excess load applied when the spacers are inserted to augment the adjacent vertebrae.

Accordingly, there is a need for improved systems that can repair damaged and/or diseased spinal tissue by augmenting the natural anatomy. There is further need for such systems and devices that can be implanted through minimally invasive surgery.

SUMMARY OF THE INVENTION

The present invention generally provides devices and methods for spinal augmentation. While the augmentation device can have a variety of designs, in one exemplary embodiment, the device includes a connector element having a superior portion and an inferior portion that is adapted to support adjacent superior and inferior vertebrae and a first superior seating member and a second superior seating member associated with the connector element. The first seating member can be adapted to receive a portion of a lamina of the superior vertebra and the second seating member can be adapted to receive a portion of the lamina of the inferior vertebra. The device can have a variety of configurations, including the connector element and the first and second seating members being unitary and the first and second seating members being separately secured to the connector element.

In another exemplary embodiment, the connector element can include a first bore adapted to receive a portion of the first seating member and a second bore adapted to receive a portion of the second seating member. The first and second seating members are able to selectively and independently slide and/or rotate within the first and second bores to facilitate positioning on a portion of the lamina of the superior and inferior vertebra and to control the flexibility properties of the device. The connector element can further include a locking mechanism to secure the position of the first and second seating elements within the first and second bores.

In another exemplary embodiment, the device can be adjusted to alter its stiffness and distraction. For example, the connector element can be a resilient arc-like member having adjacent arms. The device can include a spring member coupled to the connector element between the adjacent arms of the arc-like member. The spring member can be adapted to selectively adjust the stiffness and distraction of the adjacent arms of the connector element.

Also disclosed herein are methods for treating a spinal disorder. In one embodiment, the method includes inserting an augmentation device between adjacent superior and inferior vertebrae. The device can have a connector with a first seating element and a second seating element. The method further includes engaging a portion of a lamina of the superior vertebra with the first seating element without penetrating bone tissue and engaging a portion of a lamina of the inferior vertebra with the second seating element without penetrating bone tissue. The device can have a variety of configurations, including the connector element and the first and second seating members being unitary and the first and second seating members being separately secured to the connector element.

BRIEF DESCRIPTION OF THE DRAWINGS

The invention will be more fully understood from the following detailed description taken in conjunction with the accompanying drawings, in which:

FIG. 3A is a perspective view of an exemplary embodiment of a spinal augmentation device having a connector element;

FIG. 3B is a side view of the spinal augmentation device shown in FIG. 3A;

FIG. 3C is a side view of the spinal augmentation device shown in FIG. 3A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary devices and methods are provided for augmenting the spine. In particular, exemplary devices and methods are provided for augmenting the spine using a minimally invasive surgical technique to treat spinal conditions, including degenerative disc diseases and spinal stenosis, which can cause compression of nerves and associated leg and back pain. While the spinal augmentation device can have a variety of configurations, the augmentation devices are generally sized and configured to be affixed to portions of adjacent vertebrae in such a manner that the vertebral bodies are not penetrated or perforated. In one aspect, the augmentation devices are effective to remove some of the load from a spinal disc to reduce nerve compression and/or to allow the disc to heal. FIGS. 1A-3B illustrate exemplary embodiments of spinal augmentation devices.

Figure 1A:
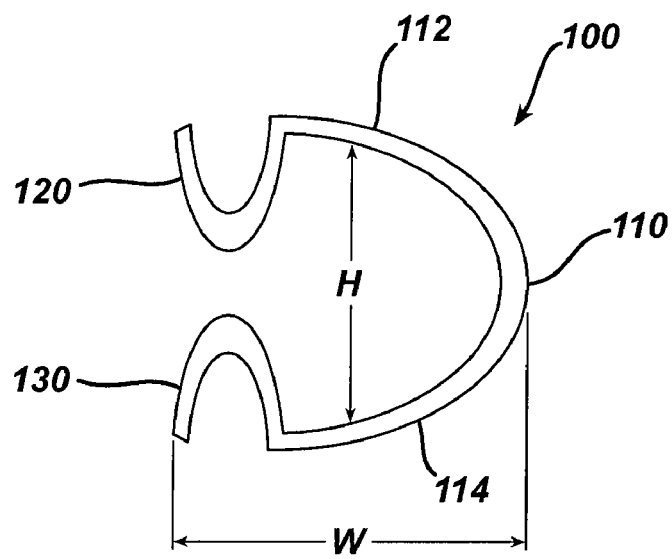
FIG. 1A is a side view of one exemplary embodiment of a spinal augmentation device having a connector element associated with a first and second seating element for receiving a portion of the lamina of superior and inferior adjacent vertebrae.
Figure 1B:
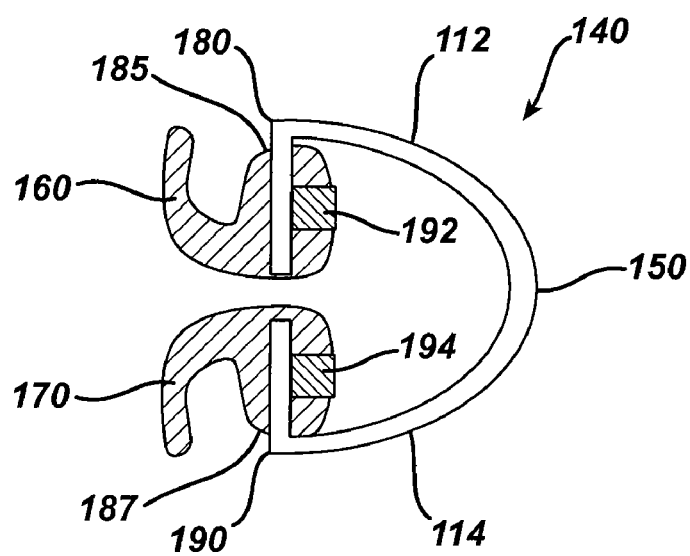
FIG. 1B is a side view of another exemplary embodiment of a spinal augmentation device having a connector element coupled to a first and second seating element for receiving a portion of the lamina of superior and inferior adjacent vertebrae.

FIGS. 1A-1B illustrate exemplary embodiments of spinal augmentation devices. Referring first to FIG. 1A, one embodiment of a spinal augmentation device 100 is shown having a connector element 110 and first and second seating elements 120, 130. While the first and second seating elements 120, 130 can be associated with the connector element 110 in a variety of ways, in one embodiment shown in FIG. 1A, the connector element 110 and the first and second seating elements 120,130 are unitary in construction.

FIG. 1B illustrates another embodiment of a spinal augmentation device 140. As shown, the device 140 is similar in configuration to the device 100 shown in FIG. 1A, except that the device 140 of FIG. 1B is not unitary. Instead, first and second seating elements 160, 170 are separately secured to a connector element 150. As shown, the first and second seating elements 160, 170 are coupled to first and second ends 180, 190 of the connector element 150 with connecting mechanisms 192, 194. In one exemplary embodiment, the first seating element includes a first bore 185 for receiving the first end 180 of the connector element 150 and the second seating element 170 includes a second bore 187 for receiving the second end 190 of the connector element 150. The connecting mechanisms 192, 194 secure the first and second ends 180, 190 within the first and second bores 185, 187 of the first and second seating elements 160, 170 to achieve coupling of the first and second seating elements 160, 170 to the connector element 150. A person skilled in the art will appreciate that the first and second seating elements 160, 170 can be secured to the connector element 150 in a variety of configurations and using a variety of connecting mechanisms, such as set screws and the like. One advantage offered by the spinal augmentation device 140 of the type shown in FIG. 1B is that the relative distance between and orientation of the first and second seating elements 160, 170 can be easily adjusted (e.g., by sliding or by rotation) to accommodate patients of different sizes and/or anatomical differences.

Augmentation devices 100, 140 are used in such a way that they can be inserted between adjacent bone structures (e.g., vertebral bodies) to distract and/or separate the bone structures in a controlled manner without penetrating or perforating the bone structures. In one embodiment, the first seating elements 120, 160 seat a portion of the lamina of a superior vertebra and the second seating elements 130, 170 seat a portion of the lamina of an adjacent, inferior vertebra. Such an arrangement allows the augmentation device to be secured between the vertebrae, without penetrating bone to alleviate some of the load placed on the disc.

One skilled in the art will appreciate that a variety of constructions can be utilized to form the augmentation devices described herein. The connector elements 110, 150 can be generally arc-like. The device should have a height (H) between adjacent arms 112, 114 that is sufficient to allow the device to span adjacent vertebral bodies while reducing the load placed on a disc. At the same time, the width (W) of the device should be as small as possible so that the device can maintain a low profile when implanted. The height (H) can be in the range of about 5 mm to about 25 mm, and more preferably about 10 mm to about 15 mm. The width (W) can be in the range of about 1 mm to about 10 mm, and more preferably about 3 mm to about 7 mm.

A variety of constructions can be utilized to form effective seating elements 120, 130, 160, 170. In one aspect, the seating elements need to only be of a size and shape that is effective to seat the lamina of a vertebral body without penetrating the vertebral body. As shown in FIGS. 1A-1B, the seating elements 120, 130, 160, 170 are hook-like members sized to seat the lamina.

The augmentation devices 100, 140 should have sufficient strength to distract or separate adjacent vertebral bodies to some degree. In one aspect, the device should have sufficient strength to be able to separate the vertebral bodies to a degree necessary to restore normal disc height. At the same time, the augmentation devices 100, 140 should have some resiliency so that some load can be bourne by the disc and so that the device does not cause intervertebral bone fusion to occur. As a general rule, the posterior column of the spine resists 20% of the compressive load while the anterior column (disc) resists the remaining 80%. Typical loads placed on the spine during average daily activities such as standing and walking are on the order of 1,000 N, 200 N (20%) of which would be placed on the posterior column where the augmentation device is implanted. The augmentation device should allow approximately 1-3 mm of displacement during such activities. Therefore, the stiffness of the device is generally in the range of about 50 N/mm to 200 N/mm.

Augmentation devices can be made from a variety of biocompatible materials, including metals, polymers, and ceramics. Exemplary materials include metals such as titanium and titanium alloys (Ti-6Al-4V), Nitinol (nickel-titanium), and stainless steel, polymeric materials such as polyetheretherketone (PEEK) and carbon fiber-reinforced PEEK, resorbable polymers such as polylactide and polyglycolide, and ceramics such as alumina and zirconia. In addition, one skilled in the art will appreciate that the seating elements 160, 170 can be made from a different material than the material used to form the connector element 150. For example, if the connector element 150 is made of a material such as a metal or metal alloy, the seating elements 160, 170 can be made from different metals or metal alloys, or from polymers or ceramics.

Various devices can be used to augment the spine while allowing for the control of the stiffness and distraction of the device. Such a design enables a surgeon to tailor the properties of the spinal augmentation device to meet the unique requirements of a given patient. For example, some patients may require an augmentation device that is initially stiffer while others require an augmentation device with a lower initial stiffness.

Figure 2A:
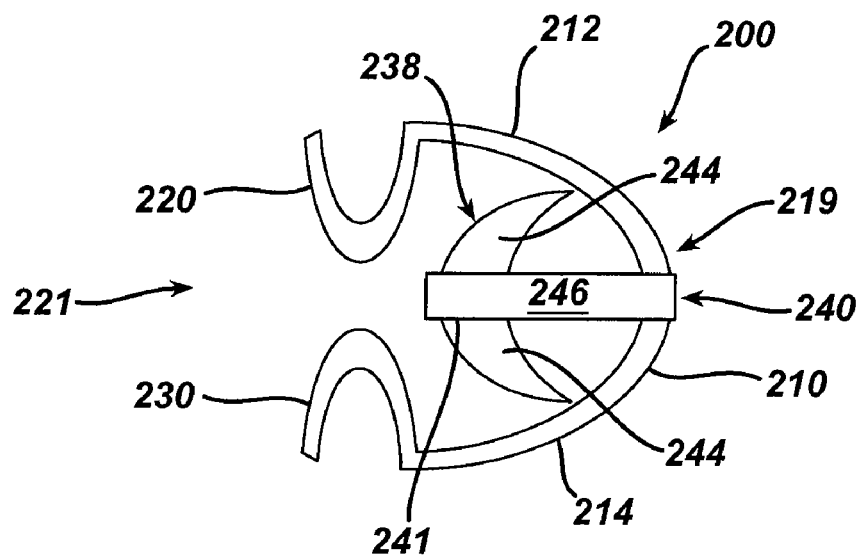
FIG. 2A is a side view of exemplary embodiment of a spinal augmentation device having a spring member coupled to a connector element between adjacent arms of an arc-like member.
Figure 2B:
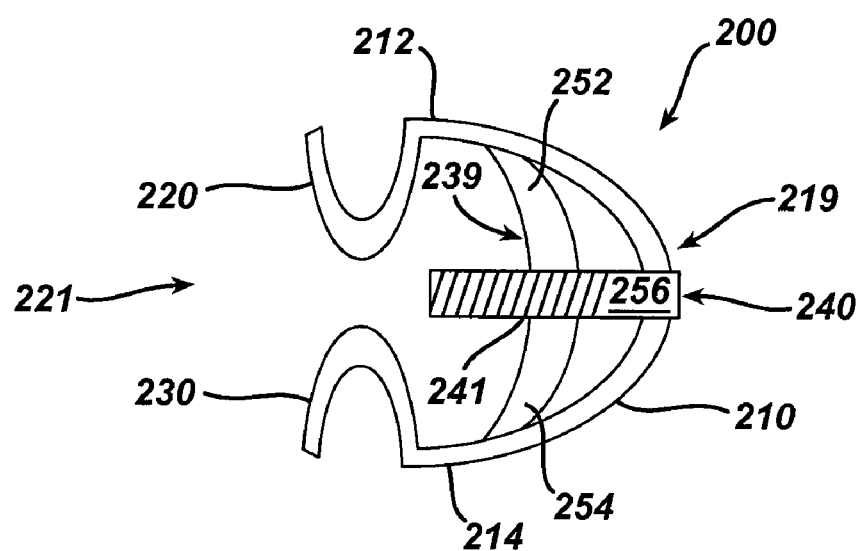
FIG. 2B is a side view of another exemplary embodiment of a spinal augmentation device having a spring member coupled to a connector element between adjacent arms of an arc-like member.

FIGS. 2A-2B illustrate exemplary embodiments of a spinal augmentation device having a spring adapted to selectively adjust the stiffness and distraction of adjacent arms of a connector element before or after implantation. The connector element can be a flexible arc-like member to allow for adjustment by the spring. A person skilled in the art will recognize that any configuration of a spinal augmentation device can utilize the spring assembly shown in FIGS. 2A-2B, including the unitary device 100 shown in FIG. 1A and the device 140 shown in FIG. 1B having the first and second seating elements separately secured to the connector element.

FIGS. 2A-2B illustrate exemplary embodiments of a device for augmenting adjacent vertebrae having a spring assembly adapted to selectively adjust the stiffness and distraction of the device. In general, a spinal adjustment device 200 can have a flexible arc-like connector element 210 with arms 212, 214 and first and second seating elements 220, 230 for receiving a portion of a lamina of superior and inferior adjacent vertebrae. The device 200 also can include a spring assembly 240 having a fixation member 246, 256 and a convex (relative to the anterior end 221 of the device) spring 238 with first and second leaflets 242, 244, or a concave (relative to the anterior end 221 of the device) spring 239 with first and second leaflets 252, 254. As illustrated, the fixation member 246, 256 is coupled to the posterior side 219 of flexible connector element 210, such as though a bore (not shown). The spring 238, 239, which may have first and second leaflets 242, 244, 252, 254 and a bore 241 formed therethrough, is adjustably coupled to the fixation member 246, 256. As further illustrated in FIGS. 2A-2B, the spring 238, 239 is centrally coupled to the fixation member 246, 256 in an adjustable manner while the ends of the leaflets 242, 244, 252, 254 contact an inner portion of arms 212, 214 of the flexible connector member 210. One skilled in the art will appreciate that the spring assembly 240 can be adjusted to control the flexibility of the device. For example, when the spring 238, 239 is advanced proximally (toward posterior side 219) along the fixation member 246, 256, the flexibility at the anterior end 221 of the device will increase. Conversely, flexibility at the anterior end 221 of the device will decrease when the spring 238, 239 is moved to a distal end of the fixation member 246, 256.

One skilled in the art will appreciate that the spring 238, 239 and the fixation member 246, 256 can be adjustably coupled in a variety of ways. By way of non-limiting example, complementary threads may be formed within bore 241 of the spring 238, 239 and on fixation member 246, 256. Alternatively, a pawl and ratchet-type mechanism can be used to facilitate the adjustable coupling of the spring 238, 239 to fixation member 246, 256. In addition, a person of ordinary skill in the art will appreciate that the spring used to adjust a spinal augmentation device can have any configuration and have any number of leaflets to allow for the adjustment of the stiffness and distraction of the device.

FIGS. 3A-5B illustrate another exemplary embodiment of a device for spinal augmentation. FIG. 3A illustrates an exemplary embodiment of a spinal augmentation device 300 having a connector element 310 with first and second bores 340, 350 disposed thereon. The first bore 340 is adapted to receive a first superior rod 320 and the second bore 350 is adapted to receive a second inferior rod 330. First and second rods 320, 330 can independently slide and rotate within first and second bores 340, 350 to adjust the placement of the device 300 between superior and inferior adjacent vertebrae. The first rod 320 can have a first seating element 322 adapted to receive a portion of a lamina of the superior vertebra and the second rod 330 can have a second seating element 332 adapted to receive a portion of a lamina of the inferior vertebra.

FIGS. 3B-3C illustrate that device 300 can be adjusted, for example during surgery, to rotate rods 320, 330 and/or change the relative position of connector element 310 along the rod. As shown in FIG. 3B, the connector element 310 is positioned toward the posterior end 319 of the device 300. As shown in FIG. 3C, the connector element 310 is positioned more toward the anterior end 321 of the device 300. One skilled in the art will appreciate that a device 300 configured as shown in FIG. 3B, with the connector element 310 positioned toward the posterior end 319 will have more flexibility at an anterior end of the device 300, where the lamina of the vertebral bodies will be seated. On the other hand, the rods 320, 330, configured as shown in FIG. 3C with the connector element 310 more anteriorly disposed, will be more rigid.

Figure 4A:
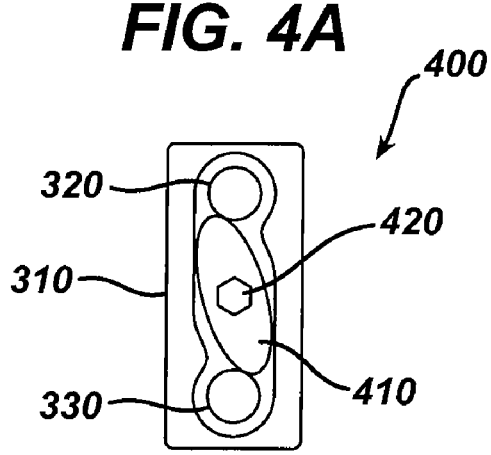
FIG. 4A illustrates an exemplary embodiment of a locking mechanism used in conjunction with the spinal augmentation device shown in FIGS. 3A-3B.
Figure 4B:
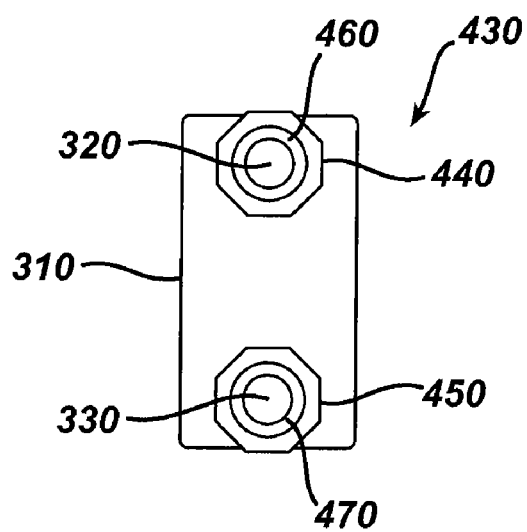
FIG. 4B illustrates another exemplary embodiment of a locking mechanism used in conjunction with the spinal augmentation device shown in FIGS. 3A-3B.

Various devices can be used to secure the first and second rods 320, 330 to the connector element 310 once the first and second rods 320, 330 have been adjusted to position the device 300 to achieve the desired augmentation of the adjacent vertebrae. FIGS. 4A-4B illustrate exemplary embodiments of locking mechanisms that can be used to secure the first and second rods 320,330 to the connector element 310. For example, FIG. 4A shows a locking mechanism having a cam 410 for securing first and second rods 320,330 to connector element 310. The cam 410 can be used to secure both the first and second rods 320, 330 simultaneously by tightening the cam 410 using a drive recess 420 disposed thereon.

FIG. 4B shows another embodiment of a locking mechanism to secure the first and second rods 320,330 to the connector element 310. The locking mechanism illustrated in FIG. 4B includes first and second male connecting elements 440, 450 which are threaded and have a bore therethrough for disposing the first and second male connecting elements 440, 450 over the first and second rods 320, 330. The first and second male connecting elements 440, 450 can be tapered to more securely hold the first and second rods 320, 330. A first nut 460 can be coupled to the first male connecting element 440 and a second nut 470 can be coupled to the second male connecting element 450 to secure the first and second rods 320, 330 to the connecting element 310. A person skilled in the art will appreciate that the locking mechanisms illustrated in FIGS. 4A-4B are exemplary and that any locking mechanism in any configuration can be used to secure the rods to the connecting element.

The connector element and rods can be made from a variety of biocompatible materials, including metals, polymers, and ceramics. Exemplary materials include metals such as titanium and titanium alloys (Ti-6Al-4V), Nitinol (nickel-titanium), and stainless steel, polymeric materials such as polyetheretherketone (PEEK) and carbon fiber-reinforced PEEK (CFRP), resorbable polymers such as polylactide and polyglycolide, and ceramics such as alumina and zirconia. One skilled in the art will appreciate that the materials used to form the connector element can be different than the materials used to form the rods. In one exemplary embodiment, the connector can be formed from a relatively rigid metal such as titanium and the rods can be formed from a more flexible material such as Nitinol, PEEK, or CFRP.

One skilled in the art will appreciate that a variety of surgical techniques can be used to implant the augmentation devices described herein. Ideally, the patient is prepared for surgery according to known procedures and the surgical site is accessed through an incision. In one aspect, the augmentation devices can be implanted though a minimally invasive surgical technique using, for example, one or more access ports. The augmentation device(s) are then installed by seating a portion of a vertebral body, such as a portion of the lamina, in the seating elements without penetrating the vertebral bodies. The vertebrae may be slightly distracted before implanting the augmentation devices, or distraction can occur through the action of the augmentation devices. Any necessary adjustments to the flexibility of the augmentation devices can be made during the surgical procedure as described above, or using a percutaneous approach at a later date.

Figure 5A:
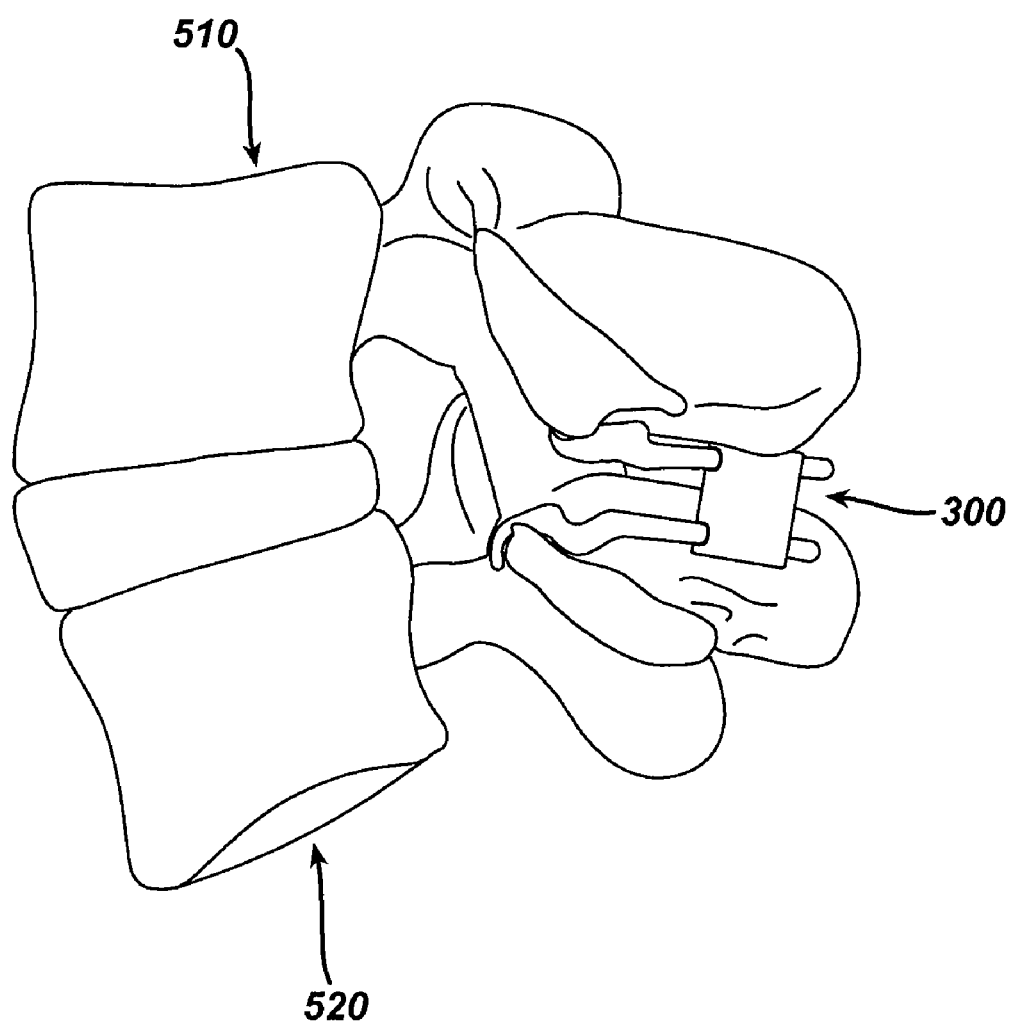
FIG. 5A is a perspective view of the spinal augmentation device shown in FIGS. 3A-3B positioned between superior and inferior adjacent vertebrae in accordance with an exemplary embodiment of the invention.
Figure 5B:
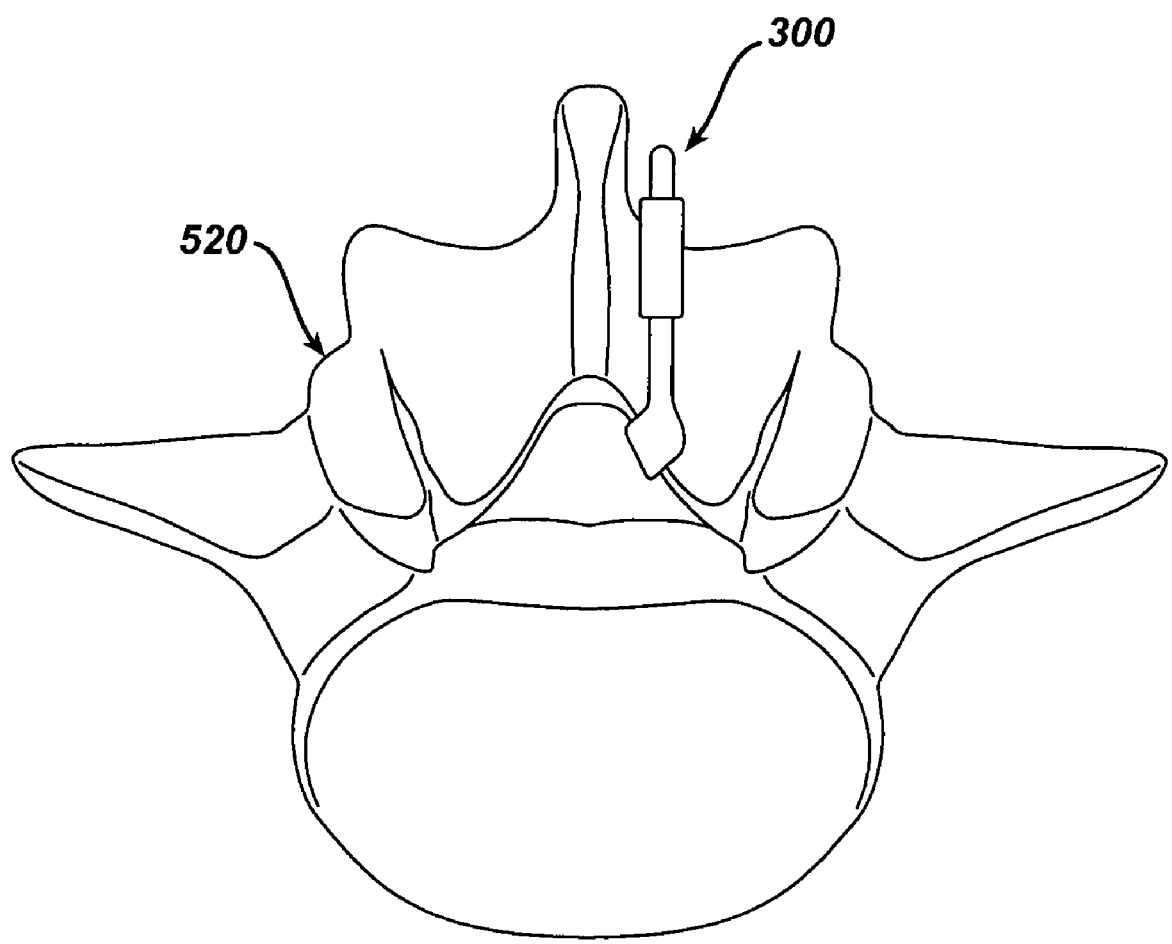
FIG. 5B is a top view of the device shown in FIG. 4A, positioned on a vertebral body.

FIGS. 5A-5B illustrate the device 300 shown in FIGS. 3A-3B positioned between superior and inferior adjacent vertebrae 510, 520. While FIGS. 5A-5B show only one device 300 positioned on one lateral side of the superior and inferior vertebrae 510, 520, a second device 300 can be positioned on the opposed lateral side. It is further understood that while the augmentation device 300 is illustrated, that augmentation devices of the types shown in FIGS. 1A-2B can be implanted in a similar manner.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal augmentation device comprising:
   a connector element configured to support adjacent superior and inferior vertebrae, the connector element being formed of a continuously concave arced member having a superior portion and an inferior portion, wherein the arced member includes a closed posterior end and an open anterior end;
   a first superior seating member associated with the connector element, the first seating member being configured to receive a portion of a lamina of the superior vertebra;
   a second inferior seating member associated with the connector element, the second seating member being configured to receive a portion of the lamina of the inferior vertebra;
   a spring member coupled to the connector element between the adjacent arms of the arced member, the spring member being configured to move anteriorly and posteriorly relative to the posterior end of the connector element to selectively adjust the stiffness and distraction of the adjacent arms;
   wherein the spinal augmentation device is sized and configured to be fully implanted in a subject between adjacent vertebral bodies to apply a distraction force to the adjacent vertebral bodies, and wherein the spinal augmentation device has a maximum height between the superior and inferior portions of the connector element and a maximum width between the posterior end and the open anterior end, and wherein the maximum height is greater than or equal to the maximum width.

2. The device of claim 1, wherein the connector element and the first and second seating members are unitary.

3. The device of claim 1, wherein the arced member is resilient and comprises adjacent arms.

4. The device of claim 1, wherein the device has an adjustable stiffness.

5. The device of claim 1, wherein the device has a stiffness in the range of about 50 N/mm to about 200 N/mm.

6. The device of claim 1, further comprising a fixation member coupled to the posterior end of the connector element and extending towards the open anterior end of the connector element.

7. The device of claim 6, wherein the spring member is adjustably coupled to the fixation member such that movement of the spring member anteriorly and posteriorly along the fixation member is configured to control the flexibility of the device.

8. A method for treating a spinal disorder comprising:
   inserting an augmentation device between adjacent superior and inferior vertebrae, the device having a connector being formed of a continuously arced member having an inferior portion associated with a first seating element and a superior portion associated with a second seating element;
   engaging an inferior portion of a lamina of the superior vertebra with the first seating element without penetrating bone tissue;
   engaging a superior portion of a lamina of the inferior vertebra with the second seating element without penetrating bone tissue; and
   adjusting at least one spring coupled to adjacent arms of the arced member to control the flexibility of the device.

9. The method of claim 8, wherein the connector and the first and second seating elements are unitary.

10. A spinal augmentation device, comprising:
    a continuously concave connector element configured to support adjacent superior and inferior vertebrae, the connector element having a superior portion and an inferior portion, wherein the connector element includes a closed posterior end and an open anterior end;
    a superior seating member associated with the superior portion of the connector element, the superior seating member configured to receive a portion of the lamina of the superior vertebra;
    an inferior seating member associated with the inferior portion of the connector element, the inferior seating member configured to receive a portion of the lamina of the superior vertebra; and
    a spring assembly extending between the superior and inferior portions of the connector element, the spring assembly comprising a spring member configured to move anteriorly and posteriorly relative to the posterior end of the connector element to selectively adjust a distraction force applied to the superior and inferior vertebrae.

* * * * *